US005520670A

United States Patent [19]
Blum

[11] Patent Number: 5,520,670
[45] Date of Patent: May 28, 1996

[54] SELF-ALIGNING OSTOMY DEVICE

[75] Inventor: John L. Blum, South Toms River, N.J.

[73] Assignee: E. R. Squibb & Sons, Inc., Princeton, N.J.

[21] Appl. No.: 463,402

[22] Filed: Jun. 5, 1995

[51] Int. Cl.⁶ .................................................. A61F 5/44
[52] U.S. Cl. ........................... 604/338; 604/342; 604/332
[58] Field of Search ..................................... 215/236, 238; 220/357; 604/332, 333, 337–344

[56] References Cited

U.S. PATENT DOCUMENTS

| 3,789,846 | 2/1974 | Babbett et al. | 604/342 |
| 4,950,261 | 8/1990 | Steer | 604/339 |
| 5,297,687 | 3/1994 | Freed | 215/236 |

Primary Examiner—Robert A. H. Clarke
Attorney, Agent, or Firm—Stuart E. Krieger

[57] ABSTRACT

The ostomy device includes a waste collection pouch and an adhesive faceplate adapted to mount the pouch to the body, adjacent the stoma. To attach the pouch to the faceplate, coupling rings, mounted respectively on each part, are aligned and snapped together. A hook member provided on the vertical centerline of the faceplate has a planar top surface which cooperates with a laterally extending elongated element located on the vertical centerline of the pouch to allow the pouch to swing to a position where the coupling rings are aligned to facilitate coupling of the rings. The hook may also have a mechanism to lock the pouch element, acting as an auxilary connection.

11 Claims, 6 Drawing Sheets

F I G. 1
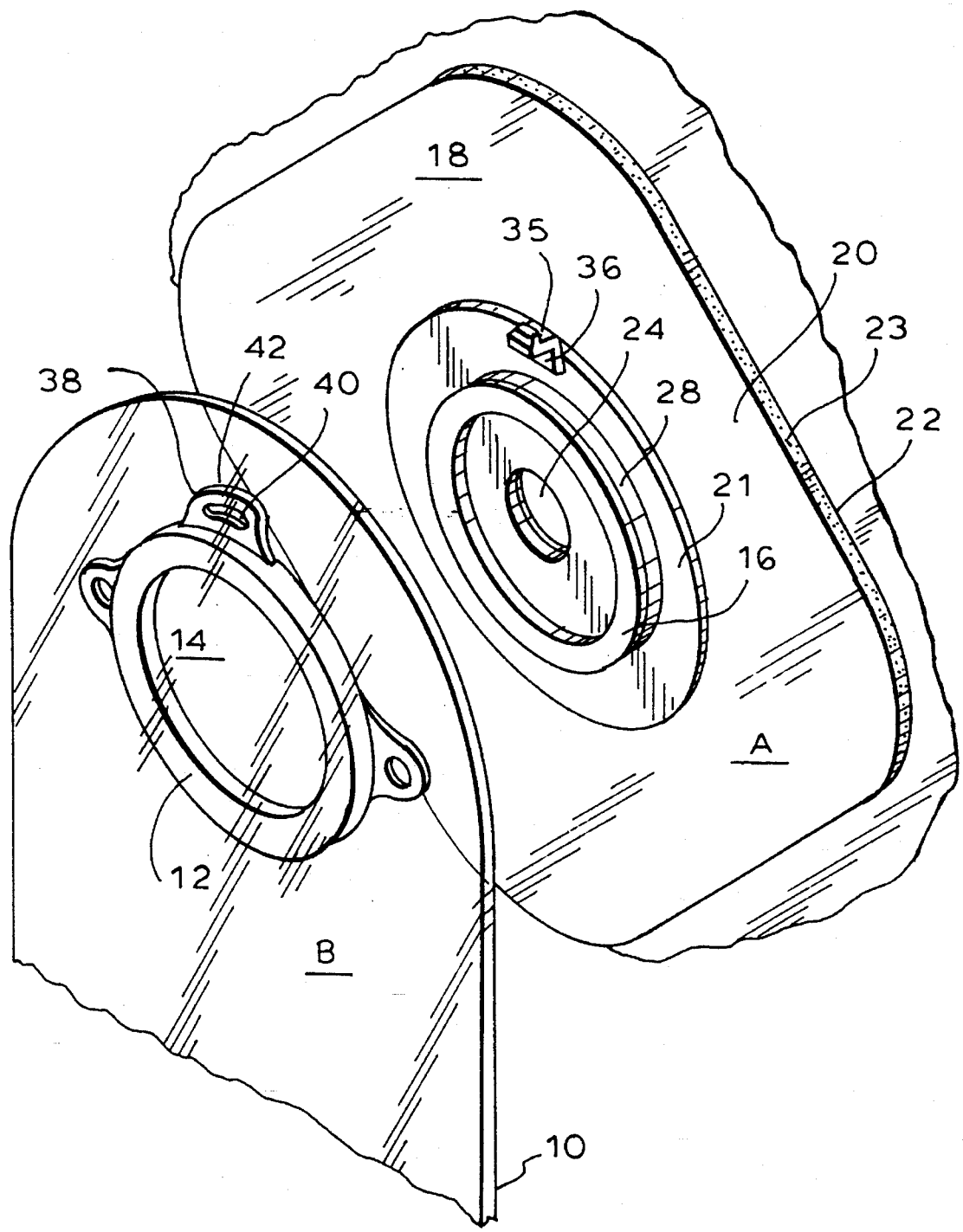

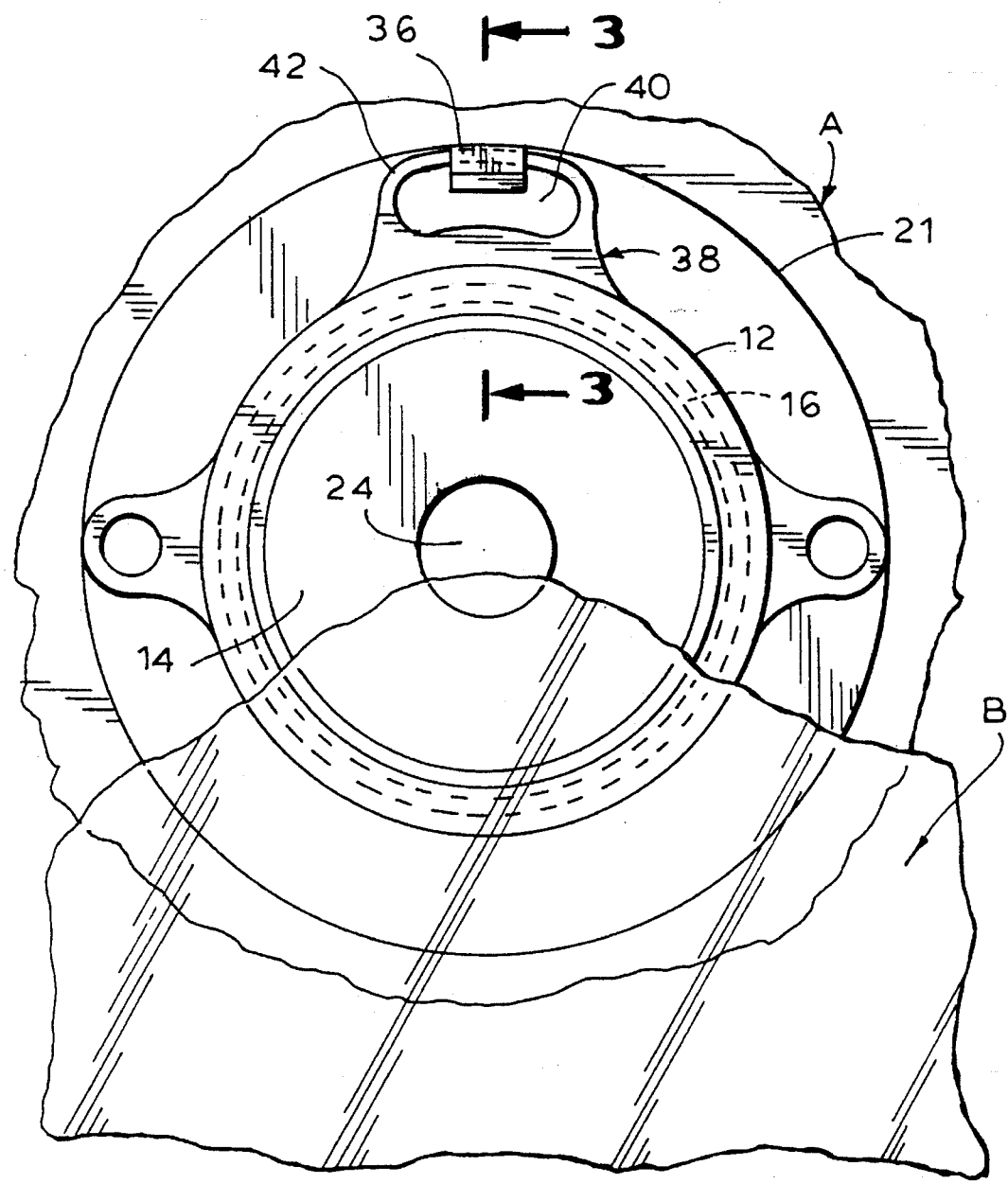
F I G. 2

FIG. 5
FIG. 6
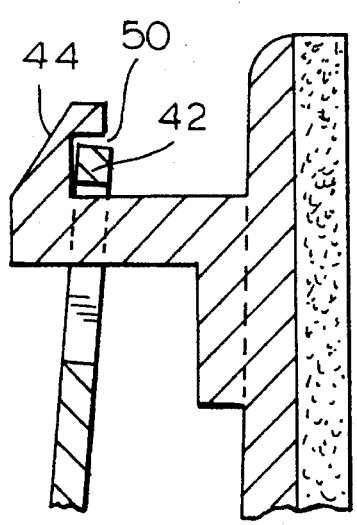
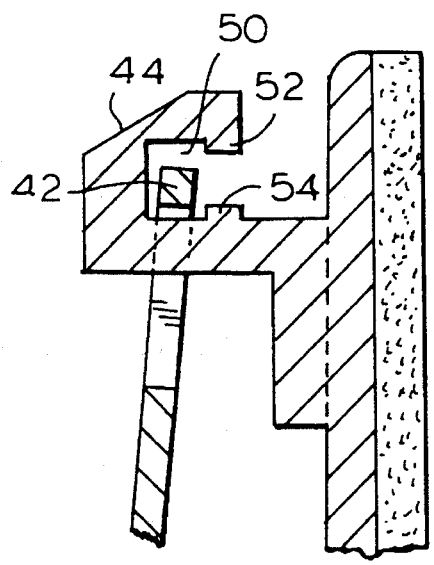
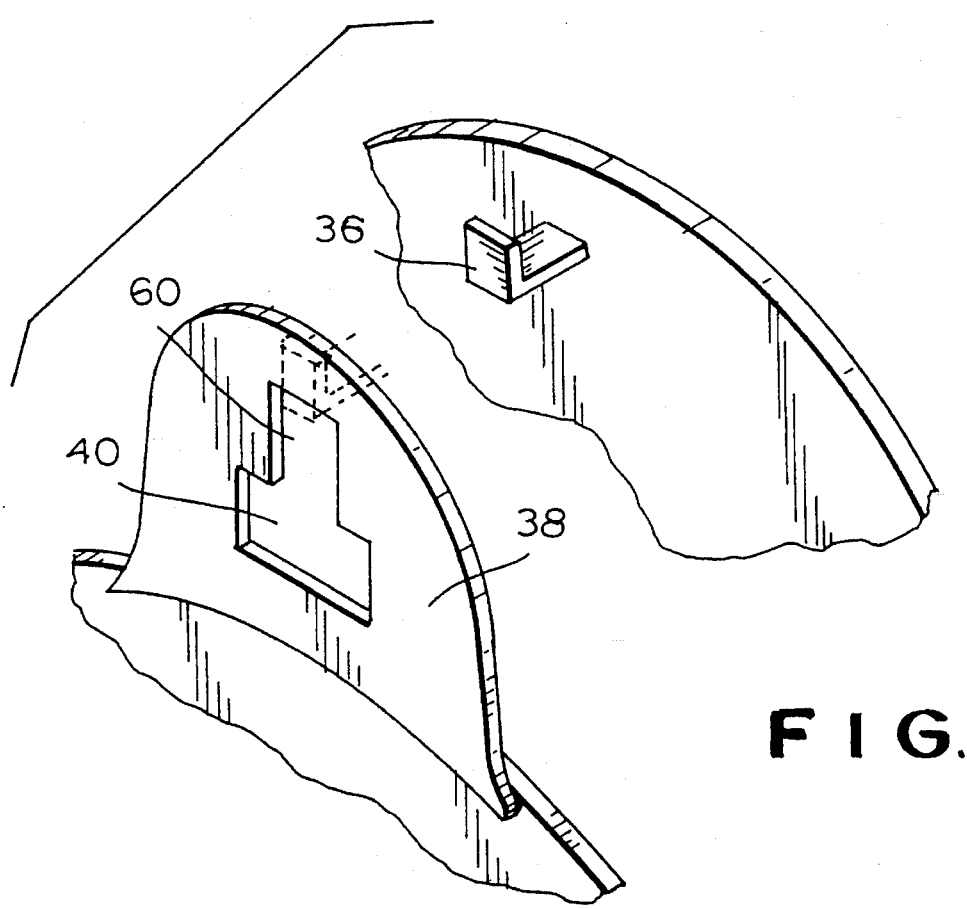
FIG. 7

SELF-ALIGNING OSTOMY DEVICE

The present invention relates to ostomy devices of the type including a faceplate adapted to be adhesively affixed to the skin surrounding the stoma and a waste collection pouch detachably mounted thereon and more particularly to such a device which includes means for facilitating alignment of the pouch and the faceplate.

Certain surgical procedures known as colostomy, ileostomy and urostomy result in an opening in the abdominal wall, called a stoma, which permits waste to discharge from the interior of a body cavity. Since the patient has no control over the waste discharge, it is often necessary for the patients who have undergone these surgical procedures to utilize an ostomy device to protect the stoma and collect the waste material as it is discharged.

Over the years, ostomy devices of a variety of different types and constructions have been utilized. Various materials and adhesives have been developed to increase the utility and wearability of same.

The basic device includes a waste collection receptacle connected to an adhesive coated faceplate which serves to mount the receptacle to the body. The receptacle typically includes first and second thin film walls which are sealed by heat welding or the like along the periphery to form the contour of a bag or pouch. An adhesive backed faceplate is designed to secure the pouch to the skin surrounding the stoma. The faceplate and pouch have openings adapted to align the stoma.

Recent improvements have extended the period during which the faceplate can be worn to be longer than normally required for a pouch to fill to capacity with waste material. Moreover, with respect to new users in particular, it may be necessary to frequently remove the device to provide access to the skin surrounding the stoma and the stoma itself. Removal of the faceplate permits observation and checking of the condition of the skin surrounding the stoma and if necessary, treatment of same. Thus, inspite of the improvements in faceplate materials and adhesives, frequent removal of the device, due to cleaning of the pouch and checking for treatement of the skin surrounding the stoma, and the stoma, can be required.

However, frequent removal of the faceplate from the skin is to be avoided. The skin surrounding the stoma is often extremely sensitive and may comprise a healing incision or scar tissue. Frequent removal of an adhesive backed faceplate can lead to skin stripping and irritation. One popular solution to this problem is to provide an ostomy device in which the pouch is removably attached to the faceplate. In this so called "two piece" device, the faceplate can remain affixed to the skin for an extended period to time, but the pouch may be removed for observation and treatment of the stoma and be replaced as necessary.

The two piece device requires a means for releasably attaching the pouch to the faceplate. One particularly successful structure takes the form of a pair of annular or ring-like rigid or semi-rigid plastic parts, one in the form of an axially extending rib and the other in the form of a channel into which the rib may be removably received and frictionally engaged.

When the faceplate is mounted to the skin, the pieces of the ostomy device are assembled by first aligning the plastic rings. A force is then applied on the exterior portion of the pouch, over the coupling rings, in a direction towards the body, along the axis of the rings, in order to snap the rings together.

One extremely commercially successful coupling ring structure is disclosed in U.S. Pat. No. 4,460,363 to Steer et al. That patent discloses a pair of coupling rings, one of which includes an axially extended rib which carries a radially outwardly extending rim and an inwardly extending sealing strip, which is extremely resilient. The other coupling ring includes a channel formed by relatively rigid spaced walls. One of the walls has an radially inwardly extending protrusion which cooperates with the radially outwardly extending rim on the rib to retain the rib within the channel. The sealing strip is deflected or deformed by channel walls, as the rib is received. The deflected sealing strip applies a force on the rib in the direction of the rim to maintain the rib securely within the channel.

In order to engage the rings, accurate alignment of the rings is required. Users with manual dexterity problems may find this difficult. In addition, the rings may be difficult for the user to see, either because of poor eyesight or obesity, making alignment a problem.

My invention overcomes these difficulties by providing a simple gravity-type self-alignment mechanism. In general, the mechanism includes a hook member having a planar top surface which is received in an opening defined by a laterally elongated element on the pouch such that the pouch may hang from the hook. With the faceplate is in place on the user and the user is in an upright position such that the faceplate is in a substantially vertical plane, the planar top surface of the hook and the elongated element on the pouch cooperate to cause the pouch to swing to a position where the centerline of the pouch ring is substantially vertical. As long as the hook member is situated above and along the centerline of the faceplate coupling ring, gravity will cause the rings to align, without any manipulation by the user. Once aligned, the rings can be coupled in the conventional manner, with no difficulty.

Another problem with two piece ostomy devices is that the coupling rings may become accidentally detached by vigorous movement of the wearer. Such detachment would normally cause the pouch to fall away from the faceplate, a result which is to be avoided. The hook in my invention may act as an auxilary locking mechanism to prevent detachment, for even greater security.

U.S. Pat. No. 4,846,820 issued Jul. 11, 1989 to Ole R. Jensen and entitled "Ostomy Device" teaches auxiliary interengaging parts which act along with the coupling rings to prevent accidental detachment and aid in supporting the pouch. However, these parts are not taught as shaped or positioned to facilitate alignment of the coupling rings. In addition, they are not provided with a locking mechanism.

It is therefore, a prime object of the invention to provide an ostomy device with a simple self-alignment mechanism.

It is another object of the present invention to provide an ostomy device wherein the self alignment mechanism includes a secondary means for locking the pouch to the faceplate, for additional security against accidental detachment.

In accordance with the present invention, an ostomy device is provided including a first part in the form of collection pouch and a second part in the form of an adhesive faceplate. Coupling rings are mounted respectively on the pouch and on the faceplace for detachably connecting the parts. Means are provided for aligning the coupling rings to facilitate engagement thereof.

The aligning means includes hook means mounted on one of the parts and hook engaging means mounted on the other part. The hook means includes a substantially planar top surface. The hook engaging means includes an opening defined, in part, by a laterally extending element. The element is adapted to be engaged by the top surface of the hook means.

Preferably, the hook engaging means comprises a tab extending from the pouch coupling ring. The tab includes a recess which is arcuate in configuration.

Means are provided on the hook means for locking the element. The locking means may include a recess in the hook means.

To these and such other objects which may hereinafter appear, the present invention relates to a self-aligning ostomy device as set forth in detail in the following specification and recited in the annexed claims, taken together with the accompanying drawings, wherein like numerals refer to like parts and in which:

FIG. 1 is an exploded isometric of a first preferred embodiment of the ostomy device of the present invention.

FIG. 2 is a plan view of the device;

FIG. 5 is a side cross-section view of showing a second form of the hook member;

FIG. 6 is a side cross-section view of a third from of the hook member;

FIG. 7 is an exploded isometric partial view of a second preferred embodiment of the present invention.

Figure 3:
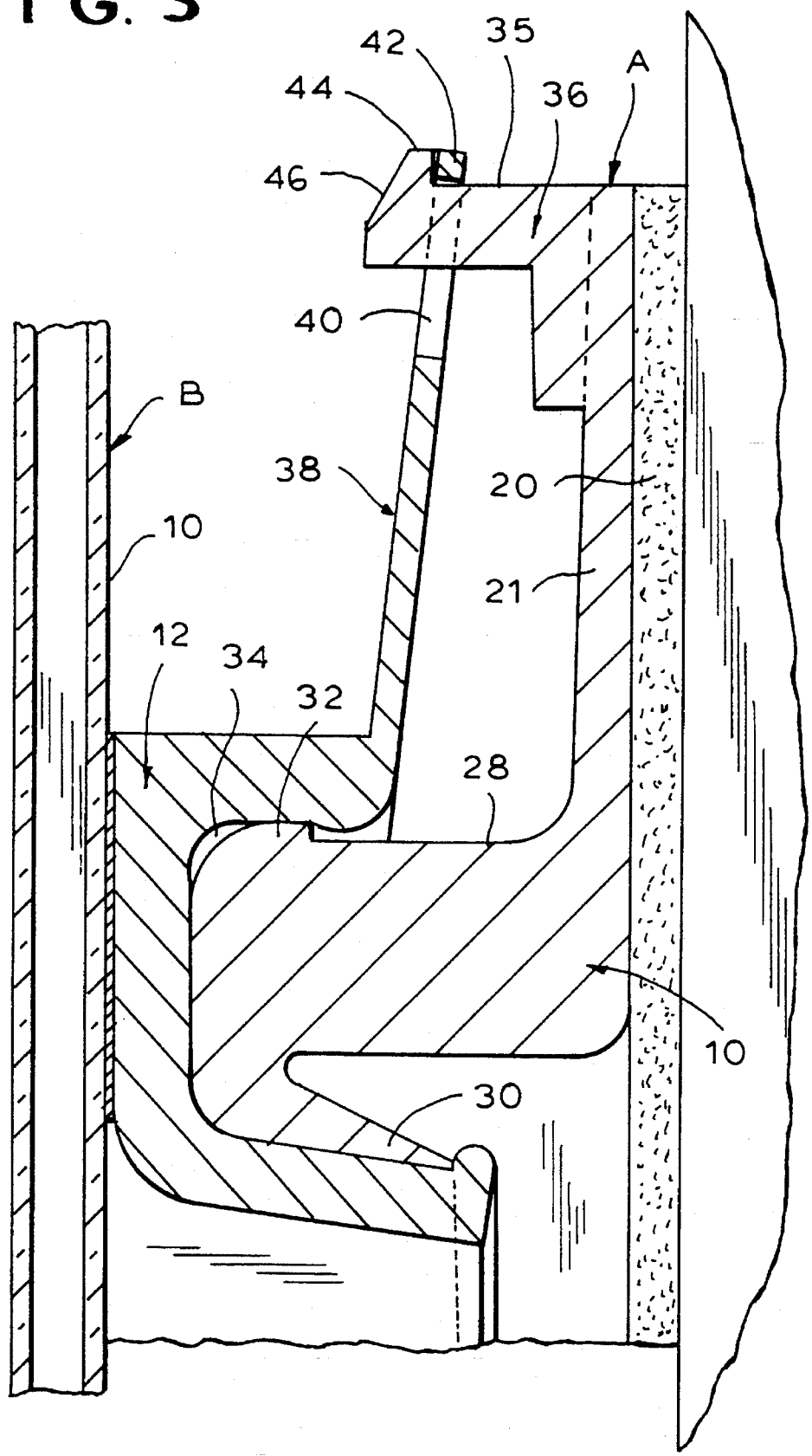
FIG. 3 is an enlarged cross-sectional view of the coupling rings after attachment.

As seen in the drawings, the device of the present invention includes an adhesive backed faceplate, generally designated A, and a waste collection pouch, generally designed B. The faceplate A and the pouch B which are illustrated are essentially as described in U.S. Pat. No. 4,400,363 to Steer et al.

The pouch B is made of two sheets of thin, flexible film. The film is fabricated from materials which posses the properties of being moisture impermeable, odor impermeable and are capable of being heat sealed or impulse welded. Suitable materials include polyethylene, copolymers of polyethylene and ethylene vinyl acetate, copolymers of polyethylene acetate, copolymers of vinyl chloride and polyvinylidene chloride and laminates thereof. The pouch walls are preferably from about 2 to 4 mils thick. The walls are sealed around their periphery to provide a waste receptable. The end of the pouch may be closed or open, as desired.

One wall of the pouch is provided with a coupling ring 12 in the form of a rigid plastic annular channel or groove which is welded or otherwise affixed to its exterior. The interior of ring 12 defines the stoma receiving opening 14 in the pouch.

Ring 12 is designed to be received over a second coupling ring 16 which is welded to the pouch side 18 of faceplate A. Coupling rings 12 and 16 sealingly inter-engage to removeably attach pouch B to faceplate A.

Pouch side 18 of faceplate A is formed by a thin flim of polymeric material 20 to which the flangle-like base 21 of coupling ring 16 is affixed. On the body side 22 of faceplate A is a layer 23 of adhesive suitable for use on human skin and capable of supporting the weight of the appliance. Layer 23 of adhesive is covered by a sheet of release paper (not shown) prior to use.

In normal use, the opening 24 in faceplate A is designed to be custom fit to the stoma by the user. This is done by enlarging the opening until it fits snugly around the stoma. The faceplate is then affixed to the body of the patient such that the adhesive layer 23 of body side 22 adheres to the skin surrounding the stoma and the stoma protrudes through the enlarged opening 24.

Figure 4:
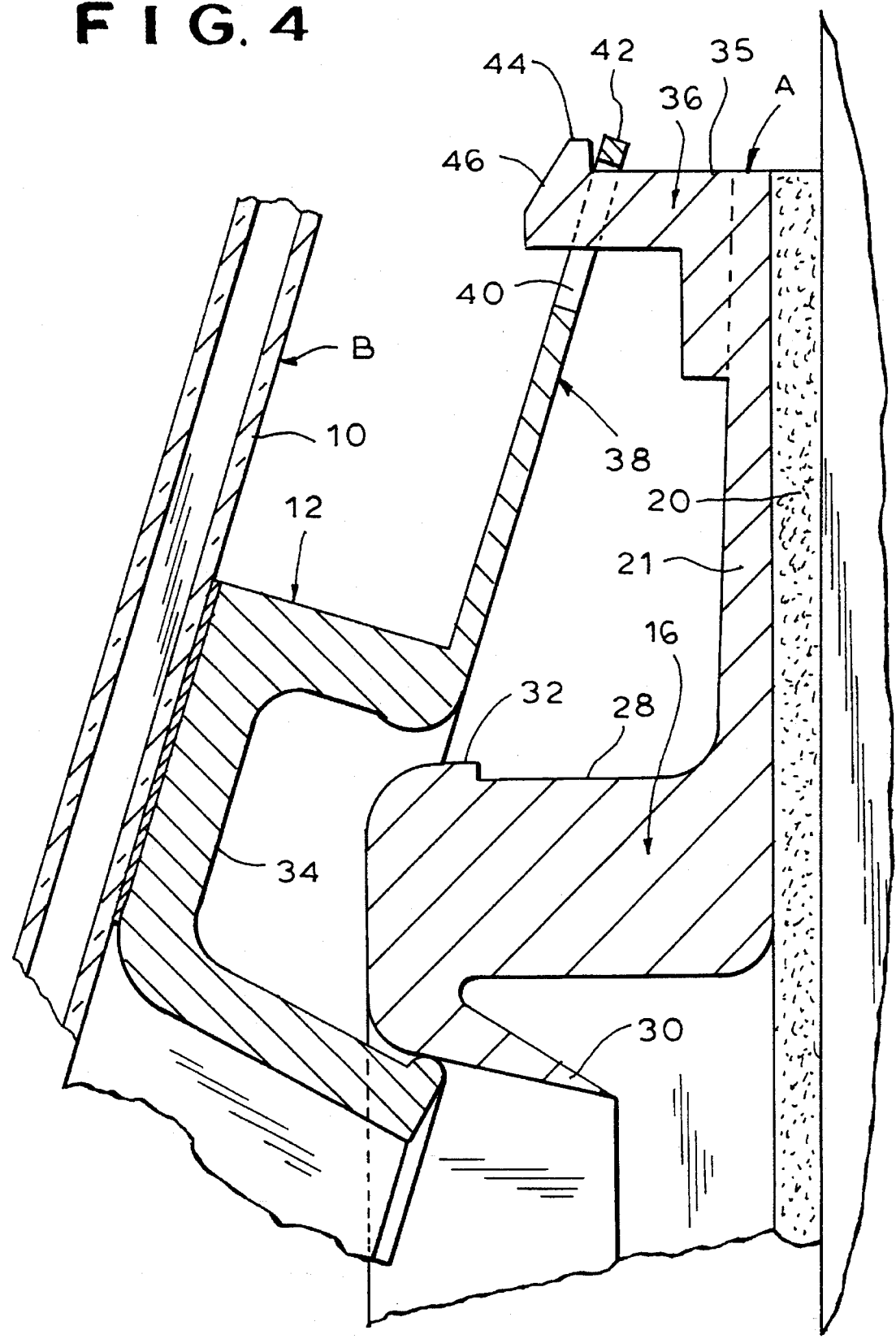
FIG. 4 is a view similar to FIG. 3 showing the coupling rings prior to attachment.

When the faceplate A is securely in place, pouch B is mounted thereto by the appropriate mating of coupling rings 12 and 16. As best seen in FIGS. 3 and 4, coupling ring 16 includes an upstanding annular wall 28 with projections 30 and 32 designed to sealingly mate with channel 34 of the coupling ring 12, which is affixed to the exterior surface of the wall 10 of pouch A. It should be appreciated that the particular configuration of the coupling rings forms no part of the present invention and should not be considered a limitation thereto.

Adhesive layer 23 of faceplate A can be formed of any pressure-sensitive adhesive suitable for use on human skin and capable of supporting the weight of the ostomy appliance. Preferably the adhesive consists of an elastomeric substance such as polyisobutylene contianing one or more hydrocolloids, as taught by Chen in U.S. Pat. No. 3,339,546, by Chen et al. in U.S. Pat. No. 4,192,785 by Pawelchak in U.S. Pat. No. 4,393,080, or it can additionally include a styrene type block copolymer as taught by Doyle et al. in U.S. Pat. No. 4,551,490. The adhesive wafer preferably will be from about 20 to 70 mils thick.

My invention involves the addition of the self-aligning means which consists of a hook member 36 situated on faceplate A, either extending from base 21 of the faceplate coupling ring 16 (FIGS. 1–7) or from annualar wall 28 of coupling ring 16 (FIG. 8), and a hook engaging part in the form of a tab 38, extending from the pouch coupling ring 12.

Tab 38 extends axially from the top of ring 12, along the vertical axis of the ring. It has a generally arcuate opening 40 defined in part by a laterally extending elongated element 42. It is situated such that it is bisected by the vertical centerline of the pouch coupling ring 12.

The central portion of the bottom surface of element 42 has substantially flat portion which extends in a direction generally perpendicular to the vertical centerline of coupling ring 12. Hook member 36 has a planar top surface 35. It is situated along the vertical centerline of the faceplate.

As seen in FIGS. 3 and 4, when hook member 36 is received in opening 40 of tab 38 such that the bottom surface of element 42 rests on the flat top surface 35 of member 36, pouch B will swing freely until gravity and the contours of the mating surfaces cause the coupling rings to align. This will occur as long as the faceplate is in the vertical position and member 36 and tab 38 are located above and along the vertical centerlines of the coupling rings. Once the coupling rings are aligned in this way, they can be snapped together, as illustrated in FIG. 4.

FIGS. 1–4 illustrate a hook member 36 with an upstanding portion 44 made of substantially resilient plastic material. Portion 44 is provided with an inclined exterior surface 46 to facilitate insertion into opening 40. Interior surface 48 of portion 44 is generally planar and parallel to the surface of base 21.

FIG. 5 illustrates another form of hook member 36 wherein upstanding portion 44 is somewhat enlarged and is provided with a recess 50 into which element 42 is frictionally retained. The resiliency of the material of which portion 44 is composed will tend to hold element 42 within recess 50.

FIG. 6 illustrated still another form of resilient portion 44, again enlarged, with a recess 50. However, in this form, the mouth of recess 50 is provided with oppositely extending parts 52, 54 which will tend to "lock" element 42 into recess 50, when same is received therein. In this way, accidental detachment of the pouch B from faceplate A will be greatly reduced.

FIG. 7 illustrates another preferred embodiment wherein the opening 40 in tab 38 is provided with a vertically upwardly extending portion 60. Portion 60 is shaped and sized to more tightly receive hook member 36.

Figure 8:
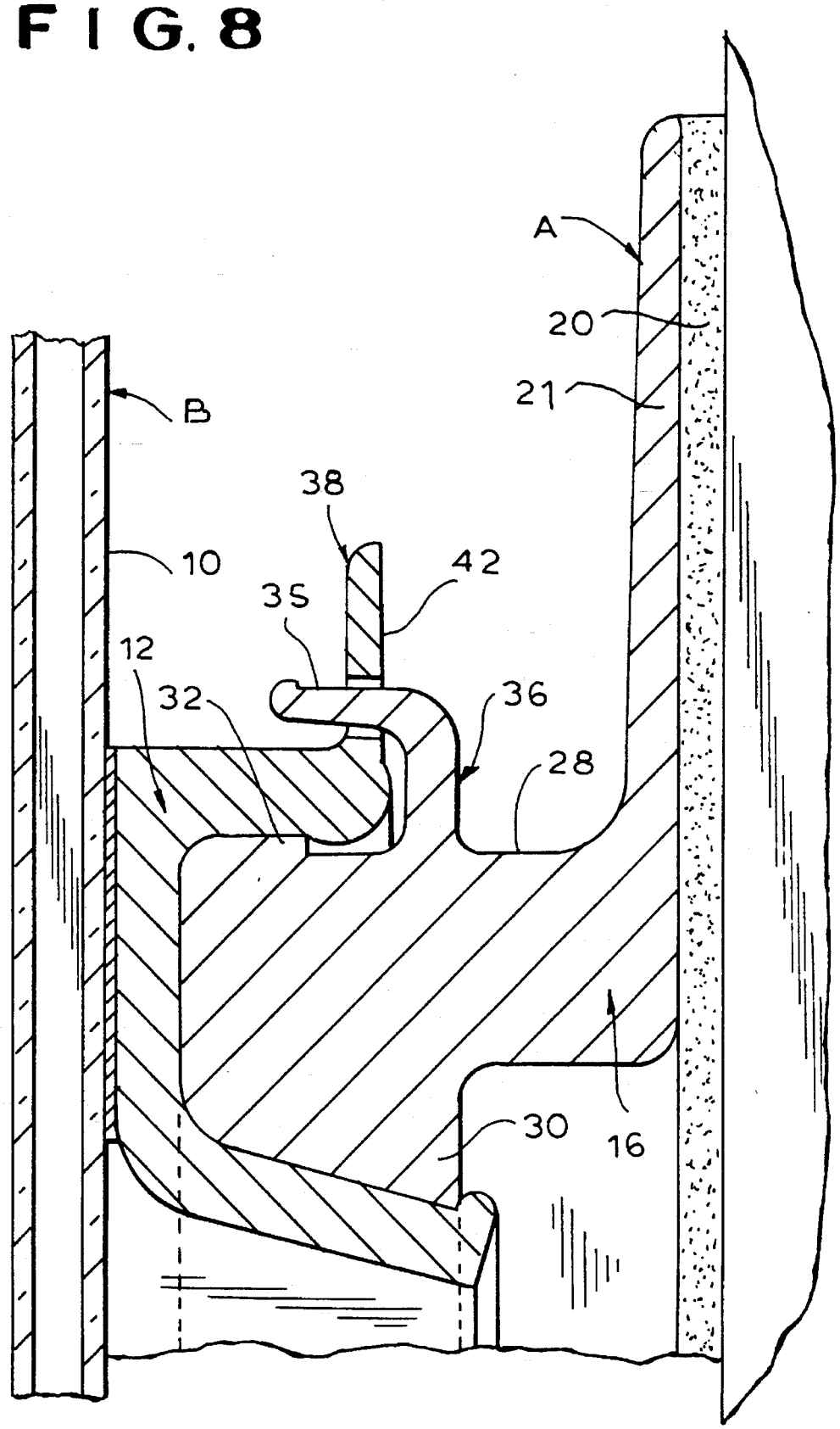
FIG. 8 is a side cross-sectional view of a third preferred embodiment of the present invention.

FIG. 8 shows another preferred embodiment of the present invention. In this embodiment, hook member 36 extends from the exterior wall 28 of ring 16, instead of base 21. More specifically, member 36 extends from wall 28 at a point thereon immediately adjacent to where the edge of ring 12 is situated, when ring 12 is received on ring 16.

It should now be appreciated that the present invention relates to a self-aligning mechanism for a two piece ostomy device in the form of a hook and a hook engaging tab. When these parts are properly shaped and located, and the hook engaging means is received on the hook, the pouch will swing to a position where the coupling rings are aligned to facilitate attachment of the pouch to the faceplate. In one embodiment, the hook is provided with a simple mechanism to lock the hook engaging tab to provide addition security against accidental detachment of the pouch from the faceplate.

Although only a limited number of preferred embodiment have been disclosed for purposes of illustration, it is obvious that many modifications and variation could be made. It is intended to cover all of these variations and modifications which fall within the scope of the present invention as defined by the following claims:

I claim:

1. An ostomy device comprising a first part in the form of a waste collection pouch and a second part in the form of an adhesive faceplate, coupling rings mounted respectively on said first part and on said second part for detachably connecting said parts, and means for aligning said coupling engagement thereof, said aligning means including hook means associated with one of said parts and hook engaging means associated with the other of said parts, said hook engaging means having a tab with an opening defined, at least in part, by a laterally extending element.

2. The device of claim 1 wherein said hook engaging means is mounted on said first part and said hook means is mounted on said second part.

3. The device of claim 1 further comprising substantially planar means on said hook means for cooperating with said element.

4. The device of claim 3 further comprising a recess in said hook means for receiving said element.

5. The device of claim 4 wherein said hook means comprises an upstanding portion and wherein said recess is situated in said upstanding portion.

6. The device of claim 3 further comprising means on said hook means for locking said element.

7. The device of claim 1 wherein said hook means extends from said coupling ring mounted on said first part.

8. An ostomy device comprising a collection pouch, an adhesive faceplate, coupling rings mounted on said pouch and on said faceplate, respectively, for detachably connecting said pouch and said faceplate, each of said coupling rings having a vertical centerline, hook means mounted on said faceplate along the vertical centerline of said faceplate coupling ring and including a surface with a substantially flat portion extending in a direction substantially perpendicular to said vertical centerline of the faceplate coupling ring, and hook means engaging means mounted on said pouch along said centerline of said pouch coupling ring and including a laterally extending element with a portion substantially perpendicular to said vertical centerline of the pouch coupling ring, said hook means engaging means having an arcuate opening, defined, at least in part, by a laterally extending element.

9. The device of claim 8 wherein said hook means includes a recess for engaging said element.

10. The device of claim 9 wherein said hook means comprises means for locking said element.

11. The device of claim 8 wherein said hook means comprises an upstanding portion with a recess adapted to frictionally engaged said element.

* * * * *